United States Patent
Zigelman et al.

(10) Patent No.: US 11,862,357 B2
(45) Date of Patent: Jan. 2, 2024

(54) ADJUSTABLE COLLIMATORS AND X-RAY IMAGING SYSTEMS INCLUDING ADJUSTABLE COLLIMATORS

(71) Applicant: Illinois Tool Works Inc., Glenview, IL (US)

(72) Inventors: Svetlana Zigelman, Minnetonka, MN (US); Brett Muehlhauser, Prior Lake, MN (US)

(73) Assignee: Illinois Tool Works Inc., Glenview, IL (US)

( * ) Notice: Subject to any disclaimer, the term of this patent is extended or adjusted under 35 U.S.C. 154(b) by 98 days.

(21) Appl. No.: 17/505,203

(22) Filed: Oct. 19, 2021

(65) Prior Publication Data

US 2022/0122747 A1 Apr. 21, 2022

Related U.S. Application Data

(60) Provisional application No. 63/094,580, filed on Oct. 21, 2020.

(51) Int. Cl.

| | |
|---|---|
| *G21K 1/04* | (2006.01) |
| *G01N 23/10* | (2018.01) |
| *G01N 23/18* | (2018.01) |
| *G21K 5/04* | (2006.01) |
| *A61B 6/06* | (2006.01) |

(52) U.S. Cl.
CPC ............... *G21K 1/04* (2013.01); *A61B 6/06* (2013.01); *G01N 23/10* (2013.01); *G01N 23/18* (2013.01); *G21K 1/043* (2013.01); *G21K 1/046* (2013.01); *G21K 5/04* (2013.01)

(58) Field of Classification Search
CPC ........... A61B 6/06; A61B 6/486; A61B 6/487; G21K 1/02; G21K 1/025; G21K 1/04; G21K 1/043; G21K 1/046; G01N 23/04; G01N 23/043; G01N 23/044;
(Continued)

(56) References Cited

U.S. PATENT DOCUMENTS

| 2,544,779 A | 3/1951 | Daly |
| 3,947,690 A | 3/1976 | Peyser |

(Continued)

FOREIGN PATENT DOCUMENTS

| FR | 635489 | 3/1928 |
| GB | 1269900 | 4/1972 |

(Continued)

OTHER PUBLICATIONS

Int'l Search Report and Written Opinion Appln No. PCT/US2021/055752 dated Feb. 24, 2022.

*Primary Examiner* — Allen C. Ho
(74) *Attorney, Agent, or Firm* — McAndrews, Held & Malloy, Ltd.

(57) ABSTRACT

An example adjustable collimator includes a housing having an aperture through which radiation is to be directed from an inlet to an outlet of the housing, a first shutter and a second shutter within the housing, a first link coupled to the first shutter, and a first yoke coupled to the housing at a pivot point and configured to pivot with respect to the housing. The first yoke may be configured to reduce an effective width of the aperture by moving the first shutter toward the second shutter via the first link when the first yoke is rotated in a first direction.

20 Claims, 8 Drawing Sheets

(58) Field of Classification Search
CPC .. G01N 23/046; G01N 23/083; G01N 23/087; G01N 23/10; G01N 23/12; G01N 23/16; G01N 23/18
USPC .............. 378/53, 54, 57, 58, 145–153, 160
See application file for complete search history.

(56) References Cited

U.S. PATENT DOCUMENTS

| | | | |
|---|---|---|---|
| 4,027,167 A | 5/1977 | Pollermann | |
| 5,991,362 A * | 11/1999 | Jones | G21K 1/04 378/150 |
| 6,148,062 A * | 11/2000 | Romeas | G21K 1/10 378/159 |
| 6,647,092 B2 * | 11/2003 | Eberhard | G21K 1/04 378/65 |
| 7,023,962 B2 * | 4/2006 | Xu | G21K 1/04 378/150 |
| 7,170,975 B2 * | 1/2007 | Distler | G21K 1/04 378/150 |
| 7,190,758 B2 * | 3/2007 | Hagiwara | A61B 6/032 378/98.12 |
| 7,440,550 B2 * | 10/2008 | Xu | G21K 1/04 378/150 |
| 7,508,918 B2 * | 3/2009 | Liu | G21K 1/04 378/150 |
| 7,688,950 B2 * | 3/2010 | Kosugi | A61B 6/06 378/146 |
| 7,945,016 B2 * | 5/2011 | Bothorel | A61B 6/14 378/197 |
| 8,085,903 B2 * | 12/2011 | Thomas | G21K 1/04 378/160 |
| 8,199,884 B2 * | 6/2012 | Junjie | G21K 1/046 378/150 |
| 8,467,495 B2 * | 6/2013 | Okada | A61B 6/542 378/151 |
| 8,824,638 B2 * | 9/2014 | Nicholson | G21K 1/04 378/150 |
| 9,036,775 B2 * | 5/2015 | Yoshikawa | A61B 6/0421 378/38 |
| 9,036,776 B2 * | 5/2015 | Sadakane | A61B 6/4476 378/38 |
| 9,138,196 B2 * | 9/2015 | Zhu | G21K 1/04 |
| 9,237,875 B2 * | 1/2016 | Pan | G21K 1/02 |
| 9,312,038 B2 * | 4/2016 | Takagaki | G21K 1/04 |
| 9,357,971 B2 * | 6/2016 | Yoshikawa | A61B 6/06 |
| 9,848,840 B2 * | 12/2017 | Ohashi | A61B 6/06 |
| 9,892,810 B2 * | 2/2018 | Kwerreveld | G21F 1/085 |
| 10,076,291 B2 * | 9/2018 | Arai | A61B 6/06 |
| 10,149,654 B2 * | 12/2018 | Melman | A61B 6/4405 |
| 10,658,089 B2 * | 5/2020 | Sharpless | G21K 1/046 |
| 10,682,103 B2 * | 6/2020 | Garlow | A61B 6/56 |
| 10,714,227 B2 * | 7/2020 | Aaron | G21K 1/02 |
| 10,799,190 B2 * | 10/2020 | Chen | A61B 6/032 |
| 10,849,576 B2 * | 12/2020 | Garlow | A61B 6/032 |
| 10,918,348 B2 * | 2/2021 | Rowland | F16M 11/2035 |
| 11,096,642 B2 * | 8/2021 | Crotty | H05G 1/36 |
| 11,103,202 B2 * | 8/2021 | Rowland | A61B 6/4476 |
| 11,147,528 B2 * | 10/2021 | Thibault | G21K 1/04 |
| 11,221,424 B2 * | 1/2022 | Vecchio | A61B 6/06 |
| 11,229,410 B2 * | 1/2022 | Turner | A61B 6/54 |
| 11,241,295 B2 * | 2/2022 | Ancar | A61B 34/20 |
| 11,530,995 B2 * | 12/2022 | Green | A61B 6/4441 |
| 11,617,553 B2 * | 4/2023 | Liu | A61B 6/5258 378/150 |
| 11,721,083 B2 * | 8/2023 | Chen | A61B 6/4429 378/63 |
| 2011/0038466 A1 | 2/2011 | Junjie | |

FOREIGN PATENT DOCUMENTS

| | | |
|---|---|---|
| JP | S5858010 | 4/1983 |
| WO | 2017066840 | 4/2017 |

* cited by examiner

ADJUSTABLE COLLIMATORS AND X-RAY IMAGING SYSTEMS INCLUDING ADJUSTABLE COLLIMATORS

RELATED APPLICATIONS

The present application claims the benefit of U.S. Provisional Patent Application Ser. No. 63/094,580, filed Oct. 21, 2020, entitled "ADJUSTABLE COLLIMATORS AND X-RAY IMAGING SYSTEMS INCLUDING ADJUSTABLE COLLIMATORS." The entirety of U.S. Patent Application Ser. No. 63/094,580 is expressly incorporated herein by reference.

BACKGROUND

This disclosure relates generally to collimators and, more particularly, to adjustable collimators and X-ray imaging systems including adjustable collimators.

Collimators are used in some radiation applications, such as, for example x-ray optics, radiation therapy, or neutron imaging. In some such examples, a collimator may be configured to reduce the size and/or control the shape of emitted radiation. Moreover, a collimator may be configured to align the radiation (e.g., limit radiation output to rays that are parallel or substantially parallel).

SUMMARY

Adjustable collimators and X-ray imaging systems including adjustable collimators, substantially as illustrated by and described in connection with at least one of the figures, as set forth more completely in the claims.

In some examples, an adjustable collimator includes a housing having an aperture through which radiation is to be directed from an inlet to an outlet of the housing, a first shutter and a second shutter within the housing, a first link coupled to the first shutter, and a first yoke coupled to the housing at a pivot point and configured to pivot with respect to the housing. The first yoke may be configured to reduce an effective width of the aperture by moving the first shutter toward the second shutter via the first link when the first yoke is rotated in a first direction.

In some other examples, an x-ray imaging system includes an x-ray generator configured to emit an x-ray beam, an image acquisition system configured to acquire a plurality of radiographs and to generate one or more images based on the radiographs, and an adjustable collimator configured to collimate the x-ray beam. The adjustable collimator may include a housing having an aperture through which the x-ray beam is to be directed from an inlet to an outlet of the housing, a first shutter and a second shutter within the housing, a first link coupled to the first shutter, and a first yoke coupled to the housing at a pivot point and configured to pivot with respect to the housing. The first yoke may be configured to reduce an effective width of the aperture by moving the first shutter toward the second shutter via the first link when the first yoke is rotated in a first direction.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

The figures are not necessarily to scale. Wherever appropriate, similar or identical reference numerals are used to refer to similar or identical components.

DETAILED DESCRIPTION

Collimators, in particular collimators for use in radiation applications, may be configured to align radiation rays (e.g., align radiation rays to be parallel or substantially parallel). In turn, the collimator may reduce scatter radiation of the emitted radiation. Moreover, collimators may reduce the size or control the shape of an emitted radiation beam.

However, conventional collimators are relatively large, which may limit the applications of collimators to relatively high energies. For example, conventional collimators may be tube shaped or otherwise within a relatively large housing. Thus, conventional collimators may be burdensome to house or store, bulky, and/or difficult to use or move. The large size of conventional collimators limits the ability to position a sample in close proximity to the face of the x-ray tube when performing geometric magnification. This limitation on positioning limits the amount of geometric magnification that is attainable using conventional collimators. Furthermore, as the collimator shutters are placed farther from the face of the x-ray generator, the cone of radiation passing through the collimator increases and requires a corresponding increase in the sizes of the shutter plates need to be to block the cone of radiation, which increases the size, weight and cost of the collimator. Additionally, conventional collimators are not adjustable. In turn, a user may need multiple, differently-sized collimators to have a collimator size or shape appropriate for a particular application. In this way, the user may have to switch the collimator used for any particular application, which may be time consuming and/or difficult. Moreover, it may be expensive to have multiple collimators on hand for the specific collimation needs of the different applications.

In contrast to conventional collimators, disclosed example collimators are both relatively small (e.g., as compared to conventional collimators) and adjustable. Therefore, disclosed example collimators discussed herein may be applicable to increased collimation applications, easier to house and store, and result in less time consumption and expense (e.g., by not having to, or not having to as frequently, change the collimator for different applications).

Figure 1:
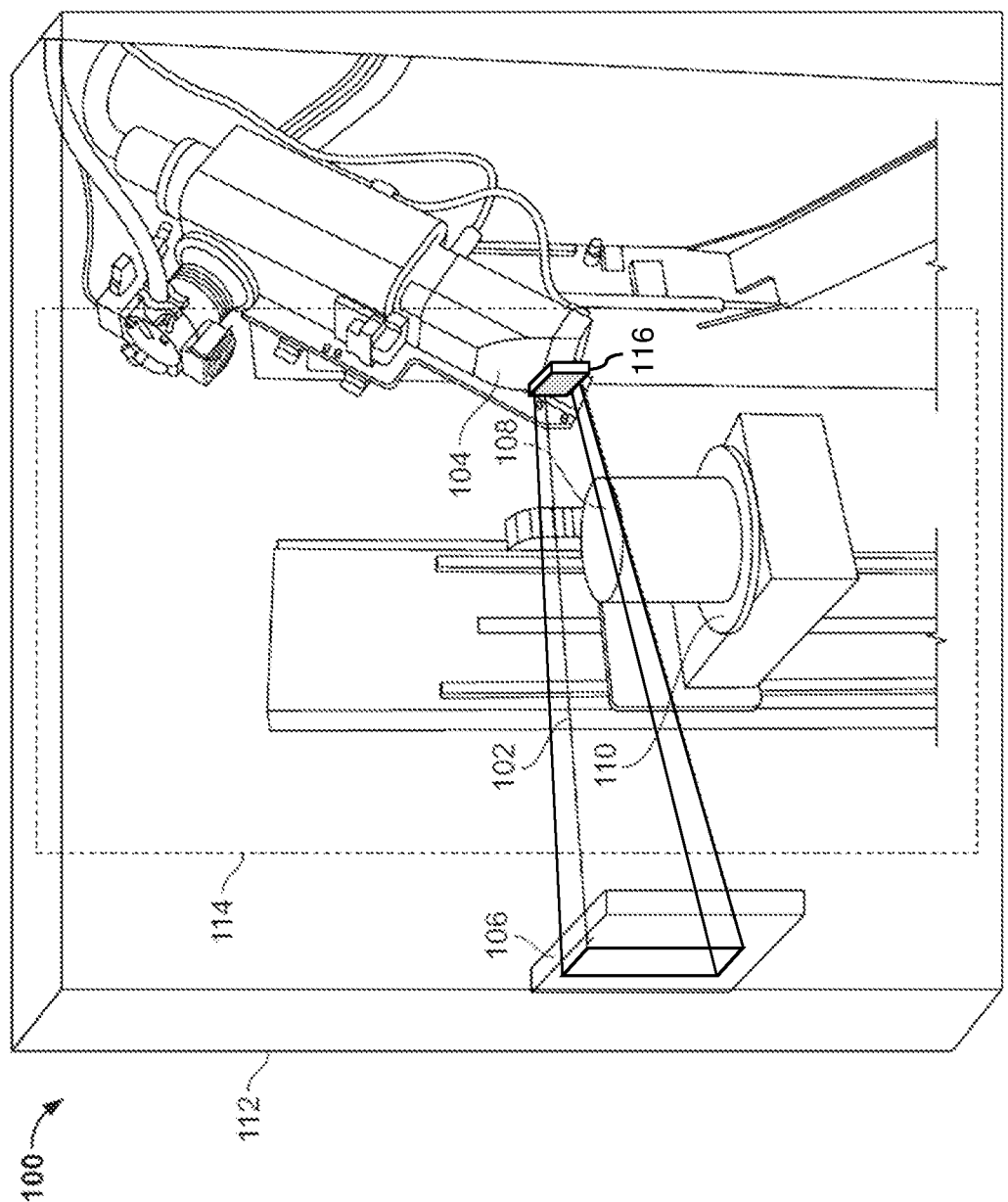
FIG. 1 illustrates an example x-ray imaging system including an adjustable collimator, in accordance with aspects of this disclosure.

FIG. 1 illustrates an example x-ray imaging system 100 that includes an adjustable collimator 116. The example x-ray imaging system 100 may be used to perform x-ray imaging, x-ray scanning (e.g., for non-destructive testing (NDT)), or the like. The example x-ray imaging system 100 is configured to direct an x-ray beam 102 emitted by an x-ray generator 104 to an image acquisition system 106 through a workpiece 108 (e.g., an object to be imaged or under test). In the example of FIG. 1, a workpiece positioner 110 holds or secures the workpiece 108, and moves and/or rotates the workpiece 108 such that the desired portion and/or orientation of the workpiece 108 is located in the path of the x-ray beam 102.

In some examples, the x-ray generator 104, the image acquisition system 106, and/or the workpiece positioner 110 may be positioned and/or reoriented using one or more actuators. Relative repositioning of the x-ray generator 104, the image acquisition system 106, and/or the workpiece positioner 110 may result in different effects, such as changing the focal length, changing the focal point, changing an unsharpness parameter, changing a magnification (e.g., a ratio of a distance between the x-ray generator 104 and the image acquisition system 106 to a distance between the x-ray generator 104 to the workpiece positioner 110 or to the workpiece 108), changing a portion of the workpiece 108 that is scanned, and/or other effects. Example implementations of the workpiece positioner 110 include a mechanical manipulator, such a platen having linear and/or rotational actuators. Other example workpiece positioners 110 may include robotic manipulators, such as robotic arms having 6 degrees of freedom (DOF).

The x-ray imaging system 100 further includes an enclosure 112, in which the x-ray generator 104, the image acquisition system 106, and the workpiece positioner 110 are enclosed. The enclosure 112 includes one or more doors 114 or other access openings to, for example, insert or remove the workpiece 108, perform servicing on any of the components within the enclosure 112, install and/or adjust the adjustable collimator 116, and/or otherwise access an interior of the enclosure 112.

The image acquisition system 106 of FIG. 1 generates digital images based on the incident x-ray beam 102 (e.g., generated by the x-ray generator 104 and directed toward the image acquisition system 106). In some examples, the image acquisition system 106 may be configured to acquire a plurality of radiographs and generate one or more images based on the radiographs. For example, the image acquisition system 106 may include a fluoroscopy detection system and a digital image sensor configured to receive an image indirectly via scintillation, and/or may be implemented using a sensor panel (e.g., an amorphous silicon panel, a CCD panel, a CMOS panel, etc.) configured to receive the x-rays directly, and to generate the digital images. In other examples, the image acquisition system 106 may use a solid state panel coupled to a scintillation screen and having pixels that correspond to portions of the scintillation screen. Example solid state panels may include amorphous silicon panels, CMOS x-ray panels and/or CCD x-ray panels. In yet other examples, the image acquisition system 106 may use a different method to generate the digital images based on the incident x-ray radiation.

The x-ray imaging system 100 further includes an adjustable collimator 116. As seen in FIG. 1, the adjustable collimator 116 may be attached to the x-ray generator 104. In some such examples, the adjustable collimator 116 may be removably attached to the x-ray generator 104. In other examples, the adjustable collimator 116 may be positioned proximate the x-ray generator 104. In any case, the x-ray radiation generated by the x-ray generator 104 may be directed through the adjustable collimator 116 to collimate the x-ray beam 102. The x-ray imaging system 100 including the adjustable collimator 116 may provide enhanced focus and/or resolution of the images generated by the image acquisition system 106. The adjustable collimator 116 may also reduce scatter of the x-ray beam generated by the x-ray generator 104 as the beam propagates.

While the example of FIG. 1 includes an x-ray generator 104 and an image acquisition system 106, in other examples the x-ray imaging system 100 may perform imaging using radiation in other wavelengths.

Figure 2:
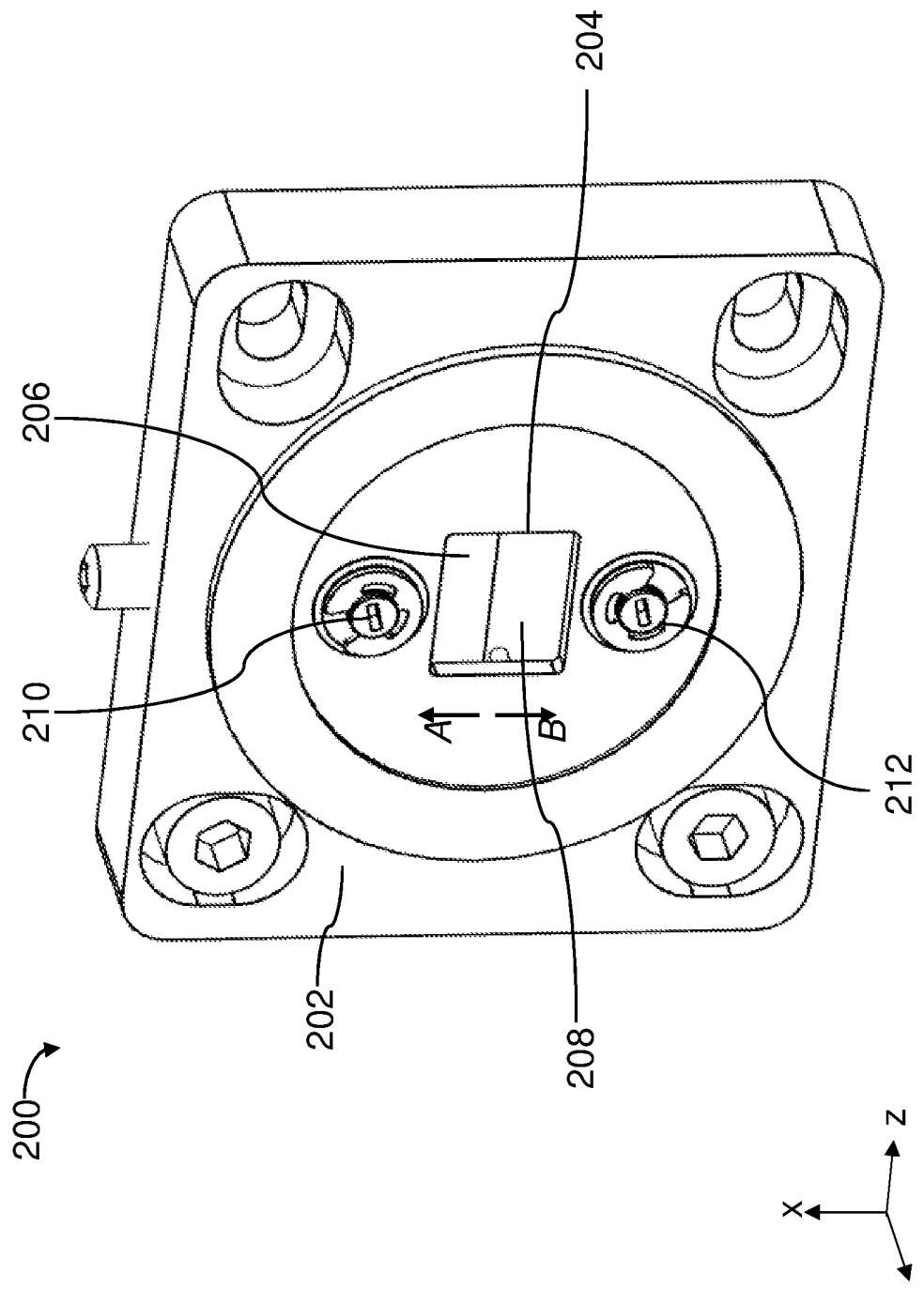
FIG. 2 is a perspective view of an example adjustable collimator that may be used to implement the adjustable collimator of FIG. 1.

FIG. 2 is a perspective view of an example adjustable collimator 200 that may be used to implement the collimator 116 of FIG. 1. The adjustable collimator 200 includes a housing 202. The housing 202 may be made of any suitable material for radiation collimation. For example, the housing 202 may be made of lead, tungsten, tantalum, molybdenum, tin, bismuth, a high density plastic, or any other suitable material.

The housing 202 may be any suitable size and/or shape. In some examples, the housing (and therefore the adjustable collimator 200) may be smaller than conventional collimators. For instance, the housing 202 may be small enough to be attached to a radiation generator or positioned proximate a radiation generator (e.g., the adjustable collimator 200 may have the same or a similar cross-sectional area as the portion of the radiation generator which emits the radiation beam).

In some examples, the width of the adjustable collimator 200 (e.g., as measured in the direction of the x-axis illustrated in FIG. 2) may be between about 1 inch and about 10 inches, between about 1 inch and about 5 inches, between about 1 inch and about 3 inches, or between about 1 inch and about 2 inches; the length of the adjustable collimator 200 (e.g., as measured in the direction of the z-axis illustrated in FIG. 2) may be between about 1 inch and about 10 inches, between about 1 inch and about 5 inches, between about 1 inch and about 3 inches, or between about 1 inch and about 2 inches; and the thickness of the adjustable collimator 200 (e.g., as measured in the direction of the y-axis illustrated in FIG. 2) may be between about 0.10 inches and about 5 inches, between about 0.1 inches and about 1 inch, between about 0.1 inches and about 0.5 inches, or between about 0.1 inches and about 0.3 inches. In other examples, the adjustable collimator 200 (e.g., the housing 202 of the adjustable collimator 200) may have different dimensions.

The housing 202 defines an aperture 204. In some examples, radiation from a radiation generator (e.g., the x-ray generator 104 of FIG. 1) is directed through the aperture 204 from an inlet to an outlet of the housing 202. In examples in which the housing 202 is configured to be attached to a source of radiation, the housing 202 may be attached to the source of radiation such that the aperture 204 is in a path of the radiation emitted by the source of radiation. The aperture 204 may be configured to collimate the radiation directed from the inlet to the outlet of the housing 202. In some such examples, collimation of the radiation reduces scatter radiation of the propagating radiation, which may reduce unintended or undesired incidence of radiation on the radiation detector.

The aperture 204 may be any suitable size and/or shape. In some examples, the width of the aperture 204 (e.g., as measured in the direction of the x-axis illustrated in FIG. 2)

may be between about 0.05 inches and about 3 inches, between about 0.1 inches and about 1 inch, between about 0.1 inches and about 0.5 inches, or between about 0.1 inches and about 0.3 inches; and the length of the aperture 204 (e.g., as measured in the direction of the z-axis illustrated in FIG. 2) may be between about 0.05 inches and about 3 inches, between about 0.1 inches and about 1 inch, between about 0.1 inches and about 0.5 inches, or between about 0.1 inches and about 0.3 inches. In other examples, the aperture 204 may have different dimensions.

The adjustable collimator 200 further includes a first shutter 206 and a second shutter 208 within the housing 202. In some examples, the first shutter 206 and/or the second shutter 208 may be configured to move (e.g., translate along the x-axis illustrated in FIG. 2) within the housing 202. In some cases, both the first and the second shutter 206, 208 may be configured to move within the housing 202. In some such examples, the first shutter 206 and the second shutter 208 may be configured to move in opposite directions of each other. For example, when the first shutter 206 is configured to translate along the x-axis in a first translation direction A, the second shutter 208 may be configured to translate along the x-axis in a second translation direction B opposite the first translation direction A. Similarly, in some such cases when the first shutter 206 is configured to translate along the x-axis in the second translation direction B, the second shutter 208 may be configured to translate along the x-axis in the first translation direction A. In this way, the first and second shutters 206, 208 may be configured to move either toward each other or away from each other. In other examples, the first and second shutters 206, 208 may be configured to move within housing 202 at different times or only one of first shutter 206 or second shutter 208 may be configured to move (e.g., with the other of the first shutter 206 or the second shutter 208 remaining stationary within housing 202). As one example, the first shutter 206 may be configured to move toward the second shutter 208. As another example, the second shutter 208 may be configured to move away from the first shutter 206.

In some examples, movement of the first shutter 206 or the second shutter 208 may be controlled manually. For example, a user may rotate a first screw 210 to adjust the first shutter 206 and/or rotate a second screw 212 to adjust the second shutter 208. In other examples, the adjustment of one of first screw 210 or second screw 212 may be configured to move both the first shutter 206 and the second shutter 208. More details with respect to the adjustment of the first shutter 206 and/or the second shutter 208 are discussed below with respect to FIG. 4. In yet other examples, the manual adjustment mechanism may be something other than a screw. In some cases, rather than the movement of the first shutter 206 and/or the second shutter 208 being controlled manually, the adjustable collimator 200 may include one or more actuators configured to drive movement of the first and/or the second shutter 206, 208.

The first and second shutters 206, 208 may be configured to adjust an effective width of the aperture 204. For example, the first and second shutters 206, 208 may be configured to substantially align with the aperture 204 such that movement of one or both of the first shutter 206 or the second shutter 208 blocks at least a portion of the aperture 204 in some configurations. In the example illustrated in FIG. 2 for instance, the first shutter 206 and second shutter 208 are in contact with each other while aligned with the aperture 204. Thus, in the example of FIG. 2, the effective width of the aperture 204 is 0. In the example of FIG. 2, the effective width of the aperture 204 can be increased by moving the first shutter 206 and the second shutter 208 away from each other (or one of the first shutter 206 or the second shutter 208 away from the other of the first shutter 206 or the second shutter 208). Conversely, while the first shutter 206 and the second shutter 208 are spaced partially or fully apart (e.g., the effective width of the aperture 204 is greater than zero), the effective width of the aperture may be decreased by moving the first shutter 206 and the second shutter 208 toward each other.

Figure 3:
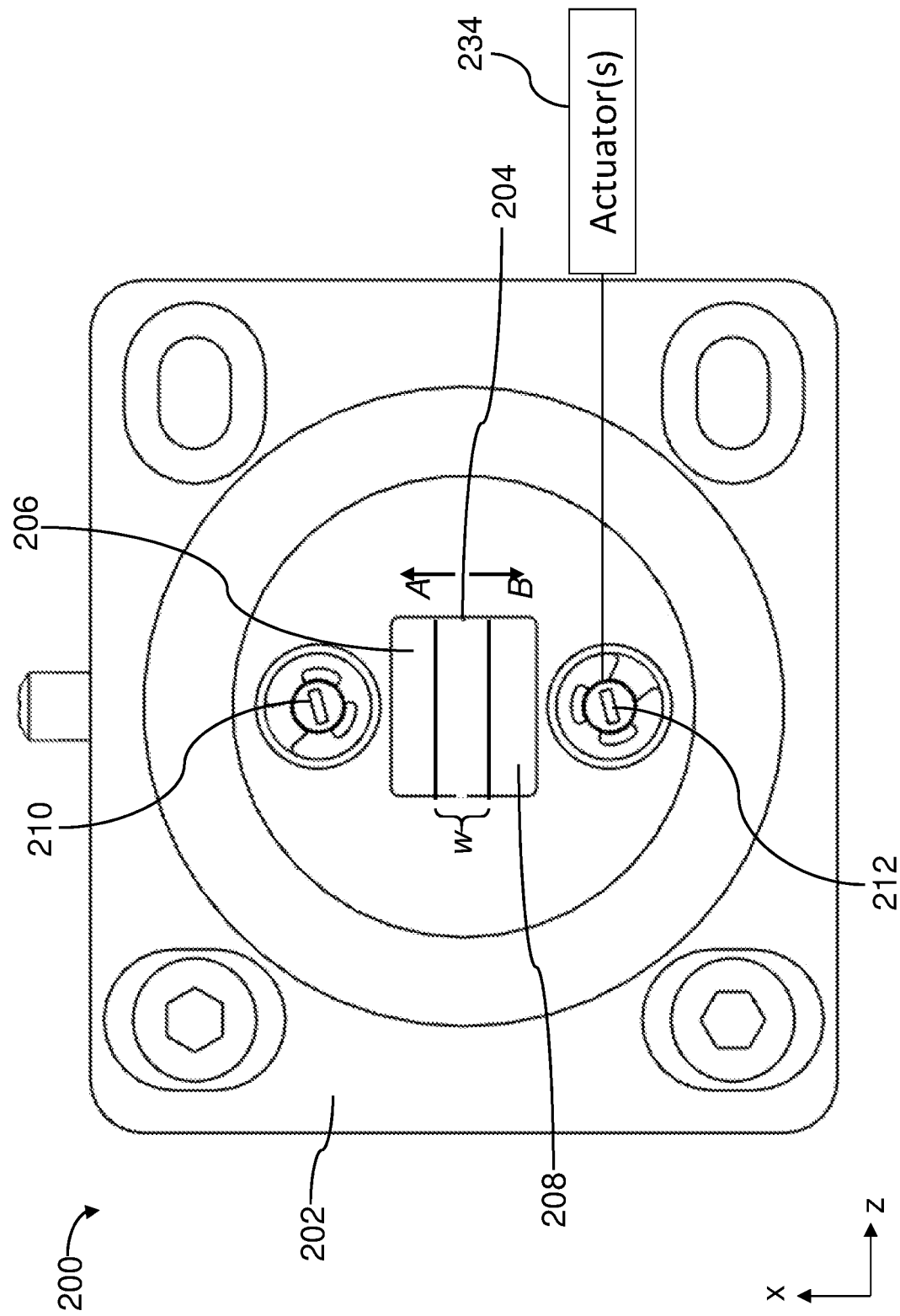
FIG. 3 is a front view of the example adjustable collimator of FIG. 2.

FIG. 3 is a front view of the example adjustable collimator 200 of FIG. 2, in accordance with aspects of this disclosure. In the example illustrated in FIG. 3, the first shutter 206 has been moved away from the second shutter 208 in the first translation direction A and the second shutter 208 has been moved away from the first shutter 206 in the second translation direction B opposite the first translation direction A (as compared to the configuration of the first and second shutters 206, 208 illustrated in FIG. 2). In turn, the effective width w of the aperture 204 has been increased (in comparison to the example of FIG. 2). In the example of FIG. 3, the first shutter 206 and the second shutter 208 are both partially blocking the aperture 204. In other examples, however, the first and/or the second shutter 206, 208 may be moved within housing 202 such that none of the first and/or the second shutter 206, 208 block the aperture 204. In examples in which neither the first shutter 206 nor the second shutter 208 block the aperture 204, the effective width w of the aperture 204 may be equal to the actual width of the aperture 204. In this way, the effective width w of the aperture 204 can be adjusted by moving one or both of the first shutter 206 or the second shutter 208 within the housing 202. In turn, the effective width w of the aperture 204 may be capable of ranging from 0 (e.g., closed by the first shutter 206 and the second shutter 208 being in contact) to the actual width of the aperture 204 (e.g., neither the first shutter 206 nor the second shutter 208 blocking any portion of the aperture 204). Thus, the collimator 200 as disclosed herein is adjustable by movement of one or both of the first shutter 206 or the second shutter 208. By being adjustable, the adjustable collimator 200 may be suitable for use with a variety of applications by enabling the size of a beam of radiation to be varied, and/or by being capable of having different levels of focus or resolution.

Figure 4:
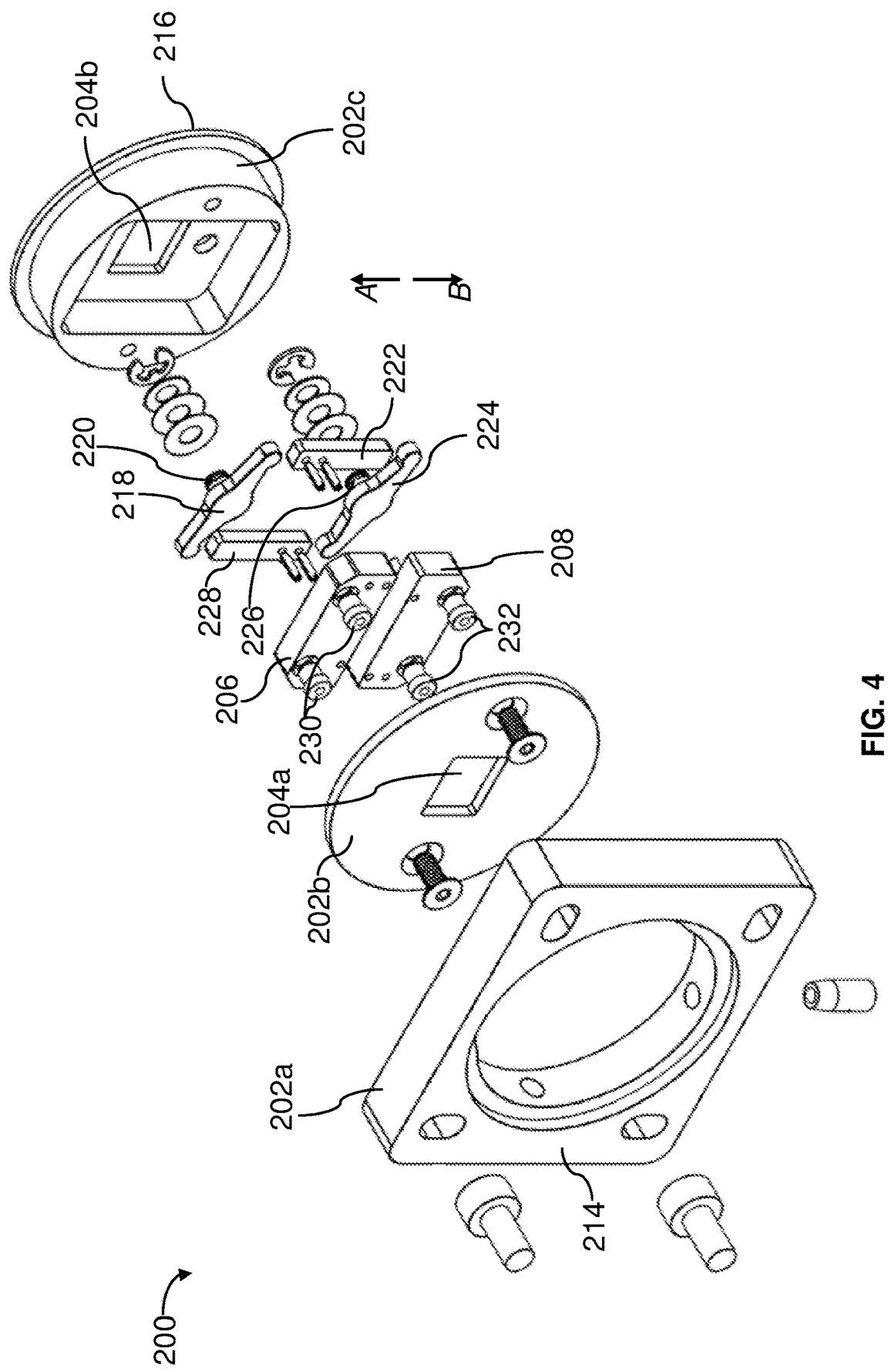
FIG. 4 is an exploded view of the example adjustable collimator of FIG. 2.

FIG. 4 is an exploded view of the example adjustable collimator 200 of FIG. 2. As seen in FIG. 4, the adjustable collimator 200 may include multiple housing components 202a, 202b, 202c that form the housing 202 when the adjustable collimator 200 is assembled. In particular, the adjustable collimator of FIG. 4 includes a first housing component 202a, a second housing component 202b, and a third housing component 202c. The housing components 202a, 202b, 202c may be coupled in any suitable manner, such as, for example, using mechanical attachment mechanisms (e.g., screws) or an adhesive. In other examples, the housing 202 may be made of fewer or more than 3 housing components. For example, in some cases, the housing 202 may include a single housing component.

The example housing component 202 may be rotated with respect to the other components of the adjustable collimator 200 to provide vertical collimation, horizontal collimation, or collimation according to any other angle. Additionally or alternatively, the example adjustable collimator 200 may be duplicated to provide multi-angle (e.g., horizontal and vertical) collimation.

In examples in which the housing 202 includes multiple housing components 202a, 202b, 202c, one or more of the housing components 202a, 202b, 202c may define all or portions of the aperture 204. For instance, in the example of FIG. 4, the second housing component 202b defines a first aperture 204a and the third housing component 202c defines a second aperture 204b. In some examples, the first aperture 204a and the second aperture 204b may be configured to align (or substantially align) when the adjustable collimator 200 is assembled. In this way, the alignment of the first aperture 204a and the second aperture 204b may form the aperture 204 that extends from an inlet 214 to and outlet 216 of the housing 202. For example, first aperture 204a may be at an inlet 214 of the adjustable collimator 200 and the second aperture 204b may be at an outlet 216 of the adjustable collimator 200. In other words, radiation may enter through the first aperture 204a and exit through the second aperture 204b.

In some such examples, the first shutter 206 and the second shutter 208 may be configured to move within the housing 202 between the first and second apertures 204a, 204b (e.g., between the second housing component 202b and the third housing component 202c). Such a configuration may enable the first shutter 206 and/or the second shutter 208 to move within the housing 202 to adjust the effective width w of the aperture 204 by moving to block both the first aperture 204a and the second aperture 204b (e.g., if the first and second aperture 204a, 204b are aligned when the adjustable collimator 200 is assembled). In this way, the second housing component 202b and the third housing component 202c may define a slot that the first and/or the second shutter 206, 208 are configured to move within. In some such examples, the first shutter 206 may include one or more plungers 230 configured to restrain movement of the first shutter 206 to follow the slot in the housing 202. Additionally, or alternatively, the second shutter 208 may include one or more plungers 232 configured to restrain movement of the second shutter 208 to follow the slot in the housing 202. The first shutter 206 and/or the second shutter 208 including one or more plungers 230, 232 may help ensure that the first and second shutter 206, 208 remain within the slot defined by the housing 202 such that movement of one or both of the first shutter 206 or the second shutter 208 results in a change of the effective width w of the aperture 204. In other words, the plungers 230, 232 may help align the first and/or second shutter 206, 208 with the aperture 204 in at least some configurations.

In examples in which the housing includes a single component or only a single aperture is defined, the first shutter 206 and the second shutter 208 may be configured to move within the housing 202 such that the first and/or second shutter 206, 208 are configured to at least partially block the aperture 204 in some positions of the first and second shutters 206, 208 to control the effective width w of the aperture 204. In some such examples, the housing 202 may still define a slot within which the first and/or second shutters 206, 208 are configured to move within.

The adjustable collimator 200 further includes a first yoke 218 coupled to the housing 202 at a first pivot point 220. The first yoke 218 may be configured to pivot with respect to the housing 202 about the first pivot point 220. In some examples, the first pivot point 220 may be at a longitudinal center of the first yoke 218. In other examples, the pivot point 220 may be located at a different position of the first yoke 218. The first yoke 218 may be configured to move the first shutter 206 to increase or decrease the effective width w of the aperture 204. For example, the first yoke 218 may be configured to move the first shutter 206 toward the second shutter 208 to reduce the effective width w of the aperture 204 when rotated in a first direction (e.g., clockwise) and/or move the first shutter 206 away from the second shutter 208 to increase the effective width w of the aperture 204 when rotated in a second direction opposite of the first direction (e.g., counter-clockwise).

In some examples, the adjustable collimator 200 may include a first link 222 coupled to the first shutter 206. In such examples, the first link 222 may be configured to move the first shutter 206 upon pivoting of the first yoke 218. For example, when the first yoke 218 is rotated in the first direction (e.g., clockwise), the first yoke 218 may push the first link 222, causing the first link 222 to move in the second translation direction B. Because the first link 222 is coupled to the first shutter 206, the first link 222 moves the first shutter 206 in the second translation direction B (e.g., toward the second shutter 208). In turn, the effective width w of the aperture 204 may be reduced.

In the example of FIG. 4, a second yoke 224 is also coupled to the housing 202 at a second pivot point 226. The second yoke 224 is configured to pivot with respect to the housing 202 about the second pivot point 226. In some examples, the second pivot point 226 may be at a longitudinal center of the second yoke 224. In other examples, the pivot point 226 may be located at a different position of the second yoke 224. The second yoke 224 may be configured to move the second shutter 208 to increase or decrease the effective width w of the aperture 204. For example, the second yoke 224 may be configured to move the second shutter 208 toward the first shutter 206 to reduce the effective width w of the aperture 204 when rotated in a first direction (e.g., clockwise) and/or move the second shutter 208 away from the first shutter 206 to increase the effective width w of the aperture 204 when rotated in a second direction opposite of the second direction (e.g., counter-clockwise).

Similar to the first link 222 and first yoke 218, in some examples in which the adjustable collimator 200 includes a second yoke 224, the adjustable collimator 200 may include a second link 228 coupled to the second shutter 208. In such examples, the second link 228 may be configured to move the second shutter 208 upon pivoting of the second yoke 224. For example, when the second yoke 224 is pivoted in the first direction (e.g., clockwise), the second yoke 224 may push the second link 228, causing the second link 228 to move in the first translation direction A. Because the second link 228 is coupled to the second shutter 208, the second link 228 moves the second shutter 208 in the first translation direction A (e.g., toward the first shutter 206). In turn, the effective width w of the aperture 204 may be reduced.

In some examples, the first yoke 218 may also be configured to move the second shutter 208. For example, the first yoke 218 may be configured to push the second link 228 in the second translation direction B upon rotation of the first yoke 218 in the second direction (e.g., counter-clockwise). In turn, the second shutter 208 coupled to the second link 228 may be moved in the second translation direction B (e.g., away from the first shutter 206) thereby increasing the effective width w of the aperture 204. Similarly, the second yoke 224 may be configured to move the first shutter 206 in the first translation direction A (e.g., away from the second shutter 208) by pushing the first link 222 when the second yoke 224 is rotated in the second direction (e.g., counter-clockwise).

In some examples, rotation of one of the first yoke 218 or the second yoke 224 may result in rotation of the other of the first yoke 218 or the second yoke 224. In turn, both of the first link 222 and the second link 228 may be pushed at substantially the same time. For example, when the first yoke 218 is rotated in the first direction (e.g., clockwise), the first yoke 218 may push the first link 222 in the second translation direction B. Movement of the first link 222 in the second translation direction B may push on the second yoke 224, causing the second yoke 224 to rotate in the first direction (e.g., clockwise). Consequently, rotation of the second yoke 224 in the first direction may push the second link 228 in the first translation direction A. Thus, movement of the first link 222 in the second translation B and movement of the second link 228 in the first translation direction A may cause the first shutter 206 and the second shutter 208 to move toward from each other simultaneously (or nearly simultaneously) to reduce the effective width w of the aperture 204.

Moreover, rotation of the first yoke 218 in the second direction (e.g., counter-clockwise) may likewise rotate the second yoke 224 in the second direction in some examples. For instance, the first yoke 218 may be rotated in the second direction (e.g., counter-clockwise), pushing the second link 228 in the second translation direction B. In turn, the second link 228 may push on the second yoke 224 to rotate the second yoke 224 in the second direction (e.g., counter-clockwise). Rotation of the second yoke 224 in the second direction may push the first link 222 in the first translation direction A. In this way, movement of the first link 222 in the first translation A and movement of the second link 228 in the second translation direction B may cause the first shutter 206 and the second shutter 208 to move away from each other simultaneously (or nearly simultaneously) to increase the effective width w of the aperture 204.

In examples in which rotation of the first yoke 218 or the second yoke 224 results in rotation of the other of the first yoke 218 or the second yoke 224, only one yoke may need to be rotated in order to move both the first shutter 206 and the second shutter 208 to reduce or increase the effective width w of the aperture 204. In turn, operation of the adjustable collimator 200 described herein may be more efficient and/or easier than other collimators.

The first yoke 218 and the second yoke 224 may be rotated in any suitable manner. In some examples, the first yoke 218 and/or the second yoke 224 may be configured to be rotated manually. For example, in some cases, the first yoke 218 may be coupled to a first screw (e.g., the first screw 210 illustrated in FIGS. 2 and 3). Additionally or alternatively, the second yoke 224 may be coupled to a second screw (e.g., the second screw 212 illustrated in FIGS. 2 and 3). Rotation of the first screw 210 or the second screw 212 (e.g., using a screwdriver) may cause rotation of the respective yoke coupled to the screw being rotated, thereby causing movement of one or both of the first shutter 206 or the second shutter 208. In other examples, other manual rotation mechanisms may be used to rotate one or both yokes. For example, one or both of the yoke(s) 218, 224 and/or one or both of the link(s) 222, 228 may extend through the housing for manual manipulation via pushing and/or pulling of the yoke(s) 218, 224 and/or the link(s) 222, 228.

In some examples, the adjustable collimator 200 may include one or more actuators 234 configured to rotate one or both of the first yoke 218 or the second yoke 224 to move the first shutter 206 and/or the second shutter 208. In some such examples, the one or more actuators 234 may be coupled to a controller configured to communicate with (e.g., command, obtain information from, etc.) the actuators 234. In some such examples, a user may be able to input a command, such as a desired effective width w of the aperture 204, and the controller may command the one or more actuators 234 to rotate the first and/or second yoke 218, 224 to cause the first and/or second shutter 206, 208 to move within the housing 202 to achieve the desired effective width w of the aperture 204. In other examples, the one or more actuators 234 may be operated in a different manner or the adjustable collimator 200 may use a mechanism other than actuators to adjust the effective width w of the aperture 204.

Figure 5:
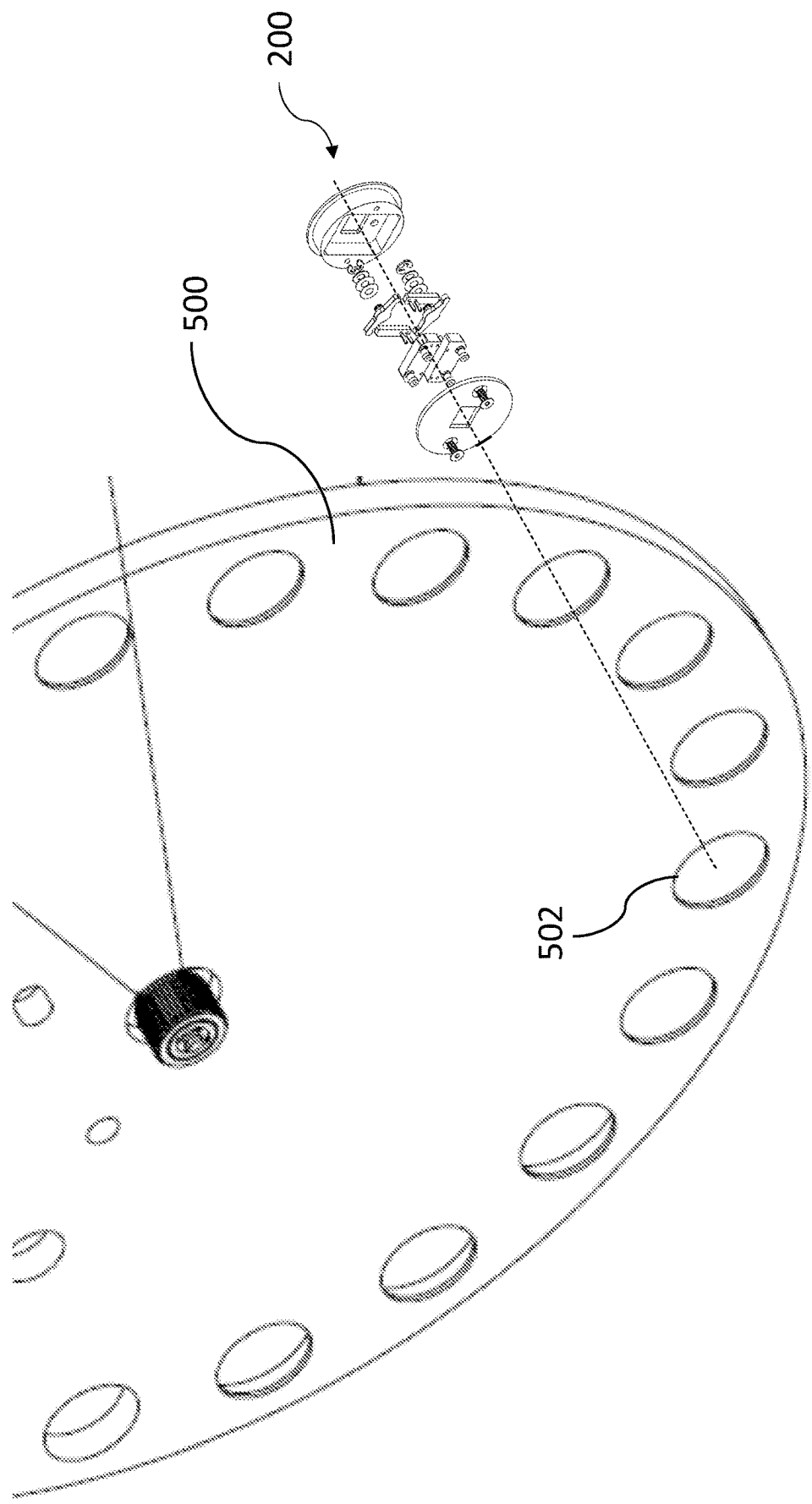
FIG. 5 is a perspective view of an example filter wheel that includes the adjustable collimator of FIG. 1.

FIG. 5 is a perspective view of an example filter wheel 500 that includes the adjustable collimator of FIG. 1. The filter wheel 500 may be placed between the x-ray generator 104 and the workpiece 108 to easily place any of multiple filters on the filter wheel 500 into a filtering position. The example filter wheel 500 may be provided with the adjustable collimator 200, in which the filter wheel 500 functions as the housing 202a to which the other components (202b, 202c, 204a-232) are coupled.

The example adjustable collimator 200 may be implemented in the filter wheel 500 using any of the orientations and/or configurations discussed above with reference to FIGS. 2-4, except that an aperture 502 in the filter wheel 500 takes the place of the housing 202a for mounting and assembling the other components.

Figure 6:
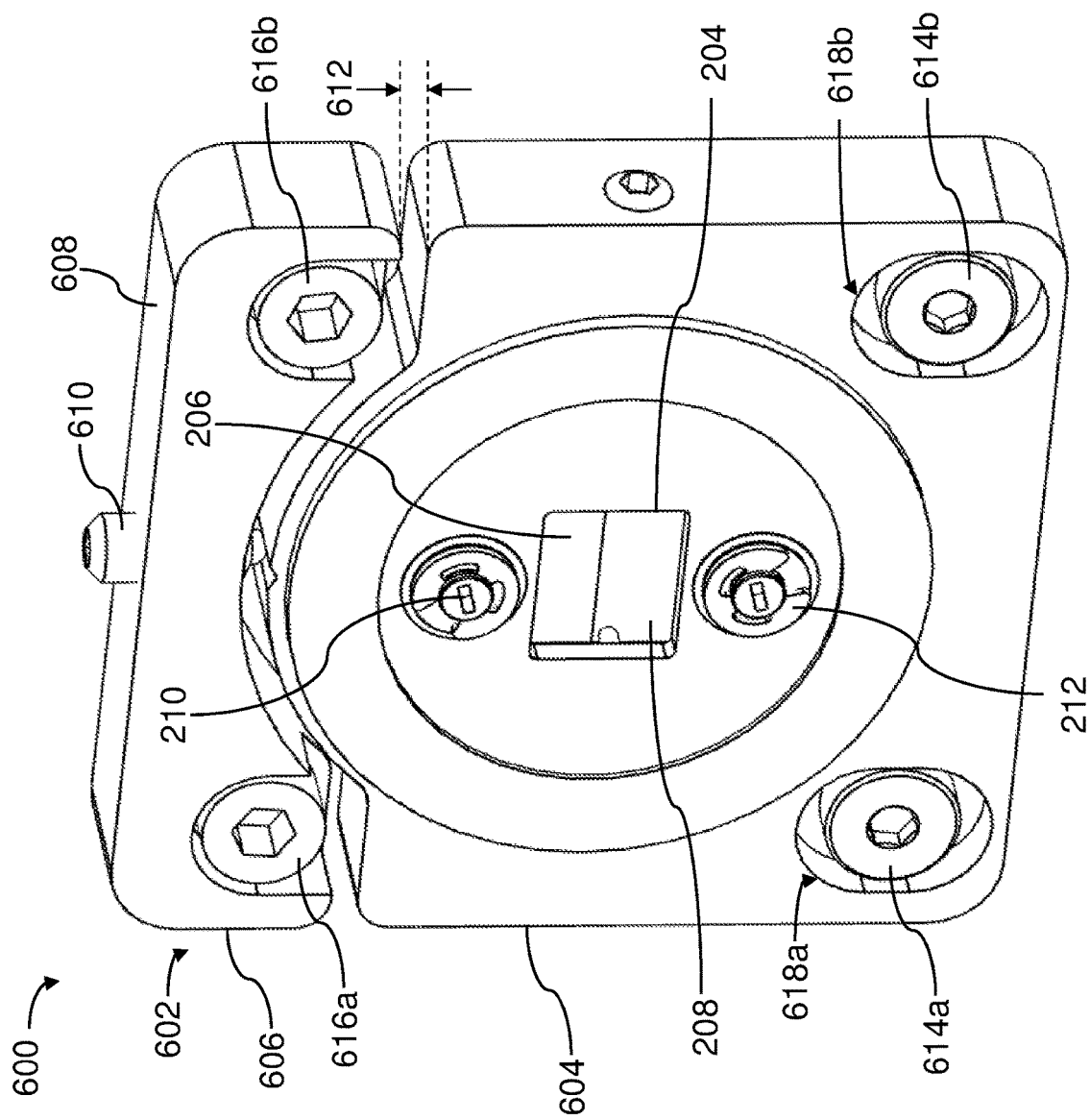
FIG. 6 is a perspective view of another example adjustable collimator having an adjustable housing and which may be used to implement the adjustable collimator of FIG. 1.
Figure 7:
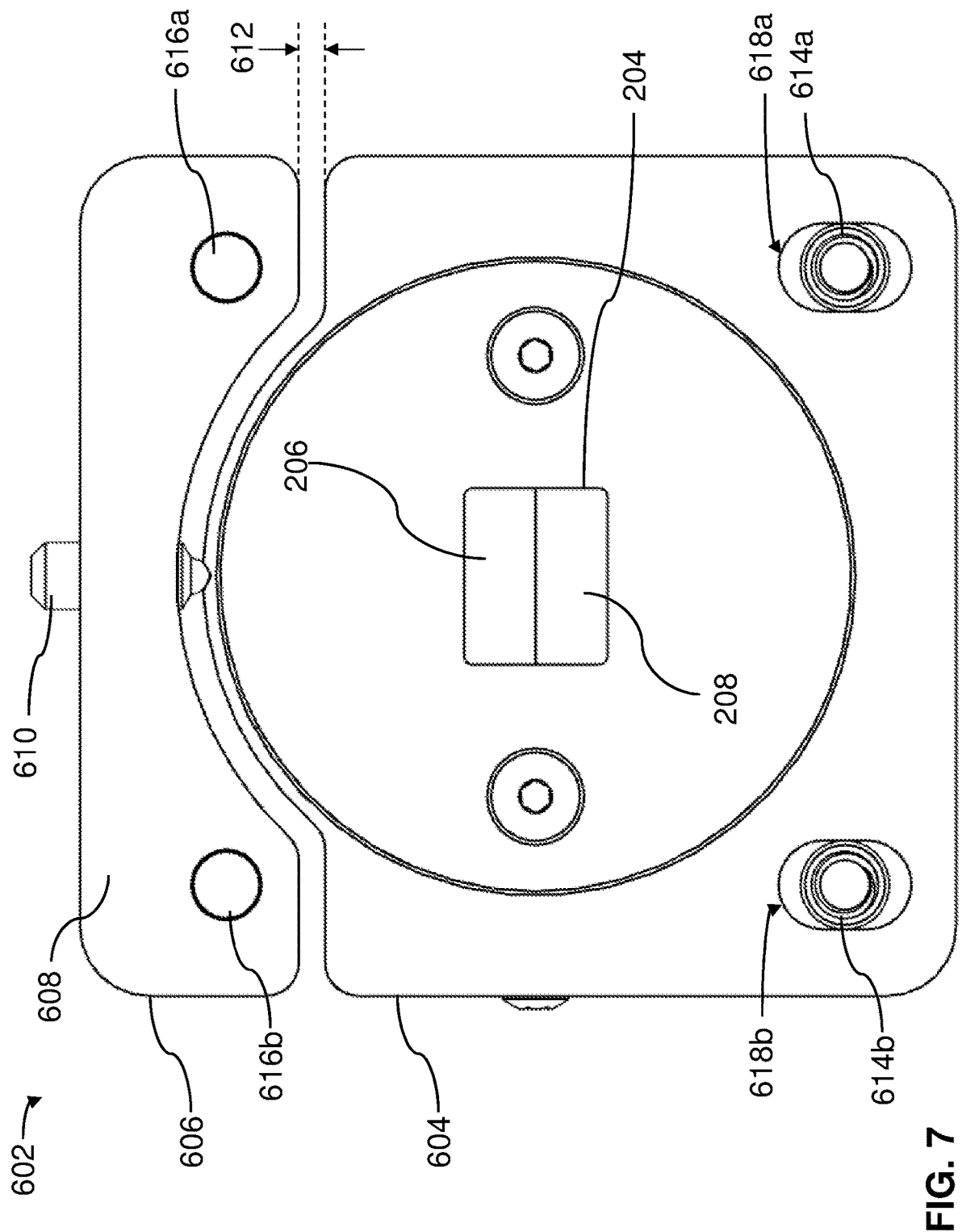
FIG. 7 is a rear elevation view of the adjustable collimator of FIG. 6.

FIG. 6 is a perspective view of another example adjustable collimator 600 having an adjustable housing 602 and which may be used to implement the adjustable collimator 116 of FIG. 1. FIG. 7 is a rear elevation view of the adjustable collimator 600 of FIG. 6. The example collimator 600 is otherwise similar to the collimator 200 of FIG. 2, and includes the aperture 204, the first shutter 206, the second shutter 208, the first screw 210, the second screw 212, the inlet 214, the outlet 216, the yoke(s) 218, 224, the pivot points 220, 226, the links 222, 228, and/or the plungers 230, 232 of FIGS. 2, 3, and 4.

The housing 602 includes a mount housing 604 and an adjustable housing component 606. The mount housing 604 may include multiple portions, similar to the housing components 202a, 202b, 202c of FIG. 3. Instead of the components 204-232 being installed in the housing 202, in the example of FIG. 6 the components 204-232 are installed in the mount housing 604. The perimeter of the mount housing 604 has a different geometry that the housing 202 to accommodate the adjustable housing component 606 while allowing installation of the components 204-232.

The adjustable housing component 606 includes an adjustment block 608 and an alignment screw 610 that adjusts a distance or gap 612 of the adjustment block 608 from the mount housing 604.

The adjustable collimator 600 is installed onto a radiation source by partially fastening the shoulder screws 614a, 614b to the radiation source to partially secure the mount housing 604b. The adjustment block 608 is also secured to the radiation source by screws 616a, 616. The mount housing 604 includes slots 618a, 618b to permit travel of the aperture 204 with respect to the shoulder screws 614a, 614b and, as a result, with respect to the radiation source. When the shoulder screws 614a, 614b and the screws 616a, 616b are installed, the alignment screw 610 may be turned to adjust the gap 612, which adjusts the location of the aperture 604 relative to the radiation source. When the aperture 204 is located in the desired position, the shoulder screws 614a, 614b may be fully secured to secure the mount housing to the radiation source.

The example collimator 600 of FIGS. 6 and 7 allow for fine adjustment of the position of the aperture 204 with respect to the radiation source to further improve alignment. In some examples, the radiation housing allows for movement of the mount housing 604 with respect to the output location of the radiation (e.g., an X-ray tube or gamma ray tube). In such examples, adjustment of the alignment screw 610 moves the mount housing 604 and, as a result, the aperture 204 with respect to the radiation output location.

Figures 8A, 8B:
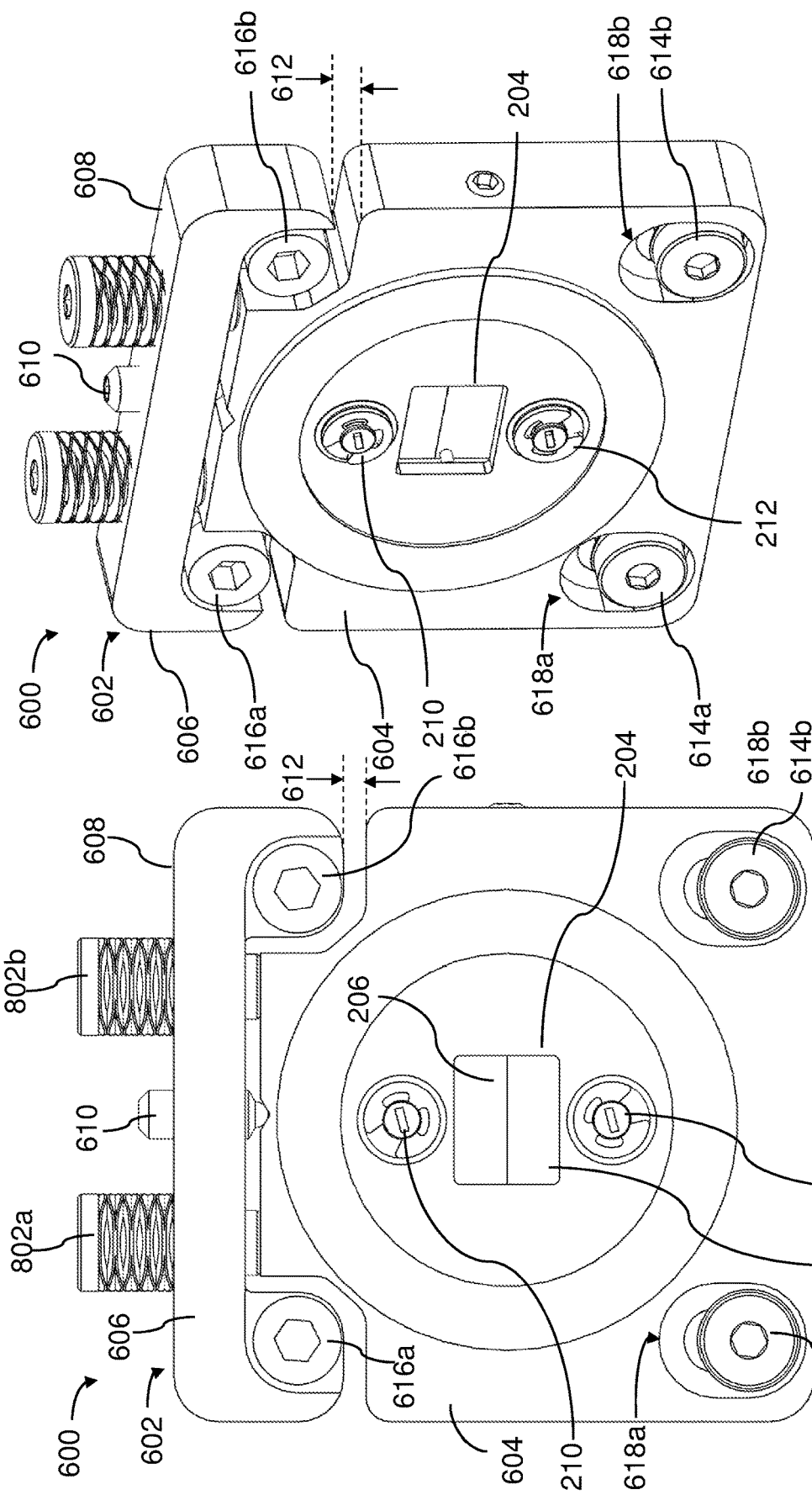
FIG. 8A is a front elevation view of another example adjustable collimator having shoulder screws to stabilize the adjustable housing component, in accordance with aspects of this disclosure.
FIG. 8B is a perspective view of the adjustable collimator of FIG. 8A.

FIG. 8A is a front elevation view of another example adjustable collimator 800 having shoulder screws 802, 804 to stabilize the adjustable housing component 606. FIG. 8B is a perspective view of the adjustable collimator of FIG. 8B. The example collimator 800 of FIGS. 8A and 8B is similar to the collimator 600 of FIG. 6, and includes the housing 602, the mount housing 604, the adjustable housing component 606, the adjustment block 608, the alignment screw 610, the shoulder screws 614a, 614b, the screws 616a, 616b, the slots 618a, 618b, the aperture 204, the first shutter 206, the second shutter 208, the first screw 210, the second screw 212, the inlet 214, the outlet 216, the yoke(s) 218, 224, the pivot points 220, 226, the links 222, 228, and/or the plungers 230, 232 of FIGS. 6 and 7.

The example collimator 800 of FIGS. 8A and 8B further includes shoulder screws 802a, 802b, which extend through the bores (not shown) in the adjustment block 608 to secure and stabilize the adjustment block 608 to the mount housing 604. The shoulder screws 802a, 802b to reduce or prevent relative rotation between the adjustment block 608 and the mount housing 604. The example adjustment block 608 is further stabilized by springs 804a, 804b, which are compressed between the shoulder screws 802a, 802b and the adjustment block 608 to reduce vibration in the adjustment block 608.

The present methods and systems may be realized in hardware, software, and/or a combination of hardware and software. The present methods and/or systems may be realized in a centralized fashion in at least one computing system, or in a distributed fashion where different elements are spread across several interconnected computing systems. Any kind of computing system or other apparatus adapted for carrying out the methods described herein is suited. A typical combination of hardware and software may include a general-purpose computing system with a program or other code that, when being loaded and executed, controls the computing system such that it carries out the methods described herein. Another typical implementation may comprise an application specific integrated circuit or chip. Some implementations may comprise a non-transitory machine-readable (e.g., computer readable) medium (e.g., FLASH drive, optical disk, magnetic storage disk, or the like) having stored thereon one or more lines of code executable by a machine, thereby causing the machine to perform processes as described herein. As used herein, the term "non-transitory machine-readable medium" is defined to include all types of machine readable storage media and to exclude propagating signals.

As utilized herein the terms "circuits" and "circuitry" refer to physical electronic components (i.e. hardware) and any software and/or firmware ("code") which may configure the hardware, be executed by the hardware, and or otherwise be associated with the hardware. As utilized herein, "and/or" means any one or more of the items in the list joined by "and/or". As an example, "x and/or y" means any element of the three-element set {(x), (y), (x, 3)}. In other words, "x and/or y" means "one or both of x and y". As another example, "x, y, and/or z" means any element of the seven-element set {(x), (y), (z), (x, y), (x, z), (y, z), (x, y, z)}. In other words, "x, y and/or z" means "one or more of x, y and z". As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" to perform a function whenever the circuitry comprises the necessary hardware and code (if any is necessary) to perform the function, regardless of whether performance of the function is disabled or not enabled (e.g., by a user-configurable setting, factory trim, etc.).

While the present method and/or system has been described with reference to certain implementations, it will be understood by those skilled in the art that various changes may be made and equivalents may be substituted without departing from the scope of the present method and/or system. For example, block and/or components of disclosed examples may be combined, divided, re-arranged, and/or otherwise modified. In addition, many modifications may be made to adapt a particular situation or material to the teachings of the present disclosure without departing from its scope. Therefore, the present method and/or system are not limited to the particular implementations disclosed. Instead, the present method and/or system will include all implementations falling within the scope of the appended claims, both literally and under the doctrine of equivalents.

What is claimed is:

1. An adjustable collimator, comprising:
   a housing having an aperture through which radiation is to be directed from an inlet to an outlet of the housing;
   a first shutter and a second shutter within the housing;
   a first link coupled to the first shutter; and
   a first yoke coupled to the housing at a pivot point and configured to pivot with respect to the housing, wherein the first yoke is configured to reduce an effective width of the aperture by moving the first shutter toward the second shutter via the first link when the first yoke is rotated in a first direction.

2. The adjustable collimator as defined in claim 1, further comprising:
   a second link coupled to the second shutter,
   wherein the first yoke is configured to increase the effective width of the aperture by moving the second shutter away from the first shutter via the second link when the first yoke is rotated in a second direction opposite the first direction.

3. The adjustable collimator as defined in claim 2, further comprising:
   a second yoke coupled to the housing at a second pivot point,
   wherein the first yoke is configured to:
      rotate the second yoke in the first direction when the first yoke is rotated in the first direction, the second yoke configured to move the second shutter toward the first shutter via the second link when rotated in the first direction; and
      rotate the second yoke in the second direction via the second link when the first yoke is rotated in the second direction, the second yoke configured to move the first shutter away from the second shutter via the first link when rotated in the second direction.

4. The adjustable collimator as defined in claim 3, wherein the first yoke is configured to push the first link and the second yoke is configured to push the second link when the first yoke and the second yoke are rotated in the first direction, and the first yoke is configured to push the second link and the second yoke is configured to push the first link when the first yoke and the second yoke are rotated in the first direction.

5. The adjustable collimator as defined in claim 3, further comprising:

an actuator configured to rotate at least one of the first yoke and or the second yoke.

6. The adjustable collimator as defined in claim 2, wherein the housing comprises a slot, wherein the first yoke and the first link are configured to move the first shutter and the second shutter within the slot in the housing.

7. The adjustable collimator as defined in claim 2, wherein the pivot point of the first yoke is at a longitudinal center of the first yoke.

8. The adjustable collimator as defined in claim 1, wherein the housing comprises a slot, wherein the first shutter comprises a plunger configured to restrain a movement of the first shutter to follow the slot in the housing.

9. The adjustable collimator as defined in claim 1, wherein the housing is configured to be attached to a source of radiation such that the aperture is in a path of radiation emitted by the source of radiation.

10. The adjustable collimator as defined in claim 1, further comprising:
an actuator configured to rotate the first yoke.

11. An x-ray imaging system, comprising:
an x-ray generator configured to emit an x-ray beam;
an image acquisition system configured to acquire a plurality of radiographs and to generate one or more images based on the plurality of radiographs; and
an adjustable collimator configured to collimate the x-ray beam, the adjustable collimator comprising:
a housing having an aperture through which the x-ray beam is to be directed from an inlet to an outlet of the housing;
a first shutter and a second shutter within the housing;
a first link coupled to the first shutter; and
a first yoke coupled to the housing at a pivot point and configured to pivot with respect to the housing, wherein the first yoke is configured to reduce an effective width of the aperture by moving the first shutter toward the second shutter via the first link when the first yoke is rotated in a first direction.

12. The x-ray imaging system as defined in claim 11, wherein the adjustable collimator further comprises a second link coupled to the second shutter, wherein the first yoke is configured to increase the effective width of the aperture by moving the second shutter away from the first shutter via the second link when the first yoke is rotated in a second direction opposite the first direction.

13. The x-ray imaging system as defined in claim 12, wherein the adjustable collimator further comprises a second yoke coupled to the housing at a second pivot point, wherein the first yoke is configured to:
rotate the second yoke in the first direction when the first yoke is rotated in the first direction, the second yoke configured to move the second shutter toward the first shutter via the second link when rotated in the first direction; and
rotate the second yoke in the second direction via the second link when the first yoke is rotated in the second direction, the second yoke configured to move the first shutter away from the second shutter via the first link when rotated in the second direction.

14. The x-ray imaging system as defined in claim 13, wherein the first yoke is configured to push the first link and the second yoke is configured to push the second link when the first yoke and the second yoke are rotated in the first direction, and the first yoke is configured to push the second link and the second yoke is configured to push the first link when the first yoke and the second yoke are rotated in the first direction.

15. The x-ray imaging system as defined in claim 13, wherein the adjustable collimator further comprises an actuator configured to rotate at least one of the first yoke or the second yoke.

16. The x-ray imaging system as defined in claim 12, wherein the housing comprises a slot, wherein the first yoke and the first link are configured to move the first shutter and the second shutter within the slot in the housing.

17. The x-ray imaging system as defined in claim 12, wherein the pivot point of the first yoke is at a longitudinal center of the first yoke.

18. The x-ray imaging system as defined in claim 11, wherein the housing comprises a slot, wherein the first shutter comprises a plunger configured to restrain a movement of the first shutter to follow the slot in the housing.

19. The x-ray imaging system as defined in claim 11, wherein the housing is configured to be at least one of attached to the x-ray generator or positioned proximate the x-ray generator, such that the aperture is in a path of the x-ray beam emitted by the x-ray generator.

20. The x-ray imaging system as defined in claim 11, wherein the adjustable collimator further comprises an actuator configured to rotate the first yoke.

* * * * *